(12) United States Patent
Kellerman et al.

(10) Patent No.: US 7,249,493 B2
(45) Date of Patent: *Jul. 31, 2007

(54) METHOD AND APPARATUS FOR MEASURING RELATIVE HUMIDITY OF A MIXTURE

(75) Inventors: Richard Kellerman, Kennett Square, PA (US); Paul H. Nielsen, Wilmington, DE (US)

(73) Assignee: Nielsen-Kellerman Co., Inc., Boothwyn, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/449,509

(22) Filed: Jun. 7, 2006

(65) Prior Publication Data

US 2006/0225486 A1     Oct. 12, 2006

Related U.S. Application Data

(63) Continuation of application No. 10/789,211, filed on Feb. 27, 2004, now Pat. No. 7,059,170.

(51) Int. Cl.
    *G01N 25/56* (2006.01)
(52) U.S. Cl. ......................................................... 73/73
(58) Field of Classification Search ..................... 73/73
    See application file for complete search history.

(56) References Cited

U.S. PATENT DOCUMENTS

| | | | |
|---|---|---|---|
| 3,926,052 A * | 12/1975 | Bechtel | ................... 73/335.05 |
| 4,217,623 A | 8/1980 | Nishino et al. | |
| 4,227,411 A | 10/1980 | Abramovich | |
| 4,282,480 A | 8/1981 | Fujito et al. | |
| 4,379,406 A | 4/1983 | Bennewitz et al. | |
| 4,419,021 A | 12/1983 | Terada et al. | |
| 4,677,415 A | 6/1987 | Howng | |
| 4,852,389 A * | 8/1989 | Mayer et al. | ................... 73/38 |
| 4,893,508 A | 1/1990 | Friedman | |
| 5,001,453 A | 3/1991 | Ikejiri et al. | |
| 5,027,077 A | 6/1991 | Yanagisawa et al. | |
| 5,028,906 A | 7/1991 | Moriya et al. | |
| 5,036,704 A | 8/1991 | Pusatcioglu et al. | |
| 5,189,902 A | 3/1993 | Groeninger | |
| 5,317,274 A | 5/1994 | Nakagawa et al. | |
| 5,369,995 A | 12/1994 | Scheinbeim et al. | |
| 5,431,040 A | 7/1995 | Aime | |
| 5,533,393 A | 7/1996 | Bonne et al. | |
| 5,565,634 A * | 10/1996 | Graessle et al. | ........... 73/865.9 |
| 5,578,753 A | 11/1996 | Weiss et al. | |
| RE35,544 E | 7/1997 | Snow | |

(Continued)

*Primary Examiner*—Hezron Williams
*Assistant Examiner*—John Fitzgerald
(74) *Attorney, Agent, or Firm*—Cozen O'Connor; Michael B. Fein

(57) ABSTRACT

A method and apparatus for measuring relative humidity of a mixture that provides a quick response time for thermal lag while affording protection to fragile sensors. In one aspect, the invention is a method for calculating the relative humidity of a mixture comprising measuring a chamber relative humidity (RHC) within a chamber enclosing an humidity sensor; measuring a first temperature (TC) within the chamber; measuring a second temperature (TA) separate from said chamber, said second temperature being the temperature of the mixture; and calculating the mixture relative humidity (RHA) based on the chamber relative humidity, a first value representing the first temperature and a second value representing the second temperature.

28 Claims, 6 Drawing Sheets

U.S. PATENT DOCUMENTS

| | | | |
|---|---|---|---|
| 5,644,080 A * | 7/1997 | Stormbom et al. ...... 73/335.05 |
| 5,672,258 A | 9/1997 | Greenblatt et al. |
| 5,677,476 A | 10/1997 | McCarthy et al. |
| 5,689,060 A | 11/1997 | Matsushima |
| 5,741,540 A | 4/1998 | Li et al. |
| 5,792,938 A | 8/1998 | Gokhfeld |
| 5,816,704 A | 10/1998 | Campbell et al. |
| 5,844,122 A | 12/1998 | Kato |
| 5,855,849 A | 1/1999 | Li et al. |
| 5,922,130 A | 7/1999 | Mosser et al. |
| 6,014,890 A | 1/2000 | Breen |
| 6,022,138 A | 2/2000 | Sonander |
| 6,048,091 A | 4/2000 | McIntyre et al. |
| 6,073,480 A | 6/2000 | Gokhfeld |
| 6,202,480 B1 | 3/2001 | Mauze et al. |
| 6,257,074 B1 | 7/2001 | Kellerman |
| 6,276,196 B2 | 8/2001 | Mauze et al. |
| 6,276,202 B1 | 8/2001 | Latarius |
| 6,418,783 B2 | 7/2002 | Sunshine et al. |
| 6,428,717 B1 | 8/2002 | Sakai et al. |
| 6,711,937 B2 * | 3/2004 | Richards et al. ........... 73/29.01 |
| 6,826,920 B2 * | 12/2004 | Wacker .................... 62/176.6 |
| 7,148,796 B2 * | 12/2006 | Joy et al. .................... 340/521 |
| 2004/0108388 A1 * | 6/2004 | Wacker .................... 236/44 C |
| 2005/0253912 A1 * | 11/2005 | Smith et al. ................. 347/102 |
| 2006/0053862 A1 * | 3/2006 | Mayer et al. ................. 73/1.06 |

\* cited by examiner

METHOD AND APPARATUS FOR MEASURING RELATIVE HUMIDITY OF A MIXTURE

CROSS-REFERENCE TO RELATED APPLICATIONS

The present invention is a continuation application of currently U.S. patent application Ser. No. 10/789,211, filed Feb. 27, 2004 now U.S. Pat. No. 7,059,170.

FIELD OF THE INVENTION

The present invention relates generally to methods and apparatus for measuring the relative humidity of a mixture.

BACKGROUND OF THE INVENTION

Hand held weather instruments exist that measure, among other variables, the relative humidity of ambient air. A humidity sensor is used to measure the relative humidity of the ambient air. While a humidity sensor is not used to measure temperature, its measurement of the relative humidity is strongly effected by the temperature of the humidity sensor itself. For example, a common type of humidity sensor determines relative humidity by determining the amount of water absorbed into a dielectric material of a capacitor. Since the ability of the dielectric material to absorb water is a function of the temperature of the dielectric material, the measurement of relative humidity is dependent upon the temperature of the humidity sensor. At higher temperatures less water can be absorbed, and at lower temperatures more water can be absorbed. Therefore, if the humidity sensor were warmer than the ambient air being measured, less water absorbs into the dielectric material and the humidity sensor responds as though the relative humidity of the ambient air were in fact lower than it actually is, resulting in an inaccurate relative humidity reading.

Inaccuracies caused by temperature differentials between the ambient air and the humidity sensor itself are especially prevalent in hand held weather instruments. Hand held weather instruments are often stored in environments, such as a user's pocket or a house, where the temperature will be much different from the temperature of the ambient air. When stored in such an environment, the humidity sensor will approach, or obtain, a thermal equilibrium with the storage environment. If the weather instrument is then removed from the storage environment and placed in the ambient air, the accuracy of the relative humidity reading of the ambient air will be compromised because the humidity sensor will not be at the same temperature as the ambient air. This is known as thermal lag. Thus, in order to obtain an accurate relative humidity reading of the ambient air with such a weather meter, one must wait until the humidity sensor reaches thermal equilibrium with the environment. However, waiting for a humidity sensor to reach thermal equilibrium with the ambient air can take a significant amount of time. Moreover, determining when thermal equilibrium is achieved can be difficult to recognize.

While methods and apparatus have been developed to compensate for thermal lag, existing methods and apparatus are unsatisfactory and/or are less than optimal. In one existing weather instrument, the problem of thermal lag is minimized by locating the humidity sensor exterior to the housing of the weather instrument so that the humidity sensor is in direct contact with the ambient air. This allows the humidity sensor to more quickly obtain thermal equilibrium with the ambient air. An example of such a weather instrument is disclosed in U.S. Pat. No. 6,257,074, which is hereby incorporated herein by reference in its entirety. However, locating the humidity sensor exterior to the housing of the weather instrument introduces a number of problems, such as exposing the humidity sensor to damage from physical contact, static discharge, and contact with contaminants, including liquid water and/or salt water. These problems are exasperated by the fact that humidity sensors are fragile and often expensive.

Thus a need exists for a method and apparatus for measuring relative humidity of a mixture that solves these and other problems.

DISCLOSURE OF THE INVENTION

An object of the present invention is to provide a method and apparatus for measuring relative humidity that compensates for thermal lag.

Another object is to provide a method and apparatus for measuring relative humidity that protects the humidity sensor.

Yet another object is to provide a method and apparatus for measuring relative humidity that provides accurate readings quickly.

Still another object is to provide a method and apparatus for measuring relative humidity that is easy and/or cost effective to manufacture.

A still further object is to provide a method and apparatus for measuring relative humidity that minimizes errors.

It is a further object of the present invention to provide a method and apparatus for measuring relative humidity that provides design flexibility.

Another object is to provide a method and apparatus for measuring relative humidity that provides accurate readings.

Still another object is to provide a method and apparatus for measuring relative humidity of an environment that does not require a user to wait for the humidity sensor to reach thermal equilibrium with the environment.

These objects and other are solved by the present invention which in one aspect is an apparatus for measuring relative humidity of a mixture comprising: a chamber having a chamber volume and an opening; a membrane covering the opening, the membrane being permeable to water vapor while impermeable to liquid water; a humidity sensor in the chamber volume for producing a first signal relating to relative humidity of the mixture within the chamber volume; a first temperature sensor for producing a second signal relating to temperature of the mixture within the chamber volume; a second temperature sensor for producing a third signal relating to temperature of the mixture at a point exterior to the chamber; and a processor coupled to the humidity sensor, the first temperature sensor, and the second temperature sensor for receiving the first, second, and third signals, the processor programmed to calculate relative humidity of the mixture at the point exterior to the chamber as a function of the first signal, the second signal, and the third signal.

Algorithms necessary to calculate the relative humidity of the mixture at the point exterior to the chamber as a function of the temperature within the chamber volume, the humidity of the mixture within the chamber volume, and the temperature of the mixture at the point exterior to the chamber are known. One such algorithm is:

$$RH_A = RH_C \left[ \frac{ew_C}{ew_A} \right] \quad (1)$$

where $RH_A$ is the relative humidity of the mixture at the point exterior to the chamber, $RH_C$ is the relative humidity of the mixture within the chamber;

$ew_c$ is the saturation vapor pressure of the mixture at the temperature of the mixture within the chamber; and $ew_A$ is the saturation vapor pressure of the mixture at the temperature of the mixture at the point exterior to the chamber.

Positioning the humidity sensor in the chamber protects the humidity sensor from physical damage and contact with contaminants. Liquids, such as liquid water and salt water, are prohibited from entering the chamber volume and contacting the humidity sensor because the membrane is impermeable to liquids. However, because the membrane is permeable to water vapor, water vapor from the mixture that is external to the chamber will permeate the membrane until an equilibrium vapor pressure is reached on both sides of the membrane. The membrane can be constructed of a microporous hydrophobic polymeric material. The membrane covers the opening of the chamber so as to isolate the chamber volume from ambient air external to the chamber.

In order for the apparatus to calculate an accurate relative humidity reading of the mixture exterior to the chamber volume, an equilibrium vapor pressure must be reached between the mixture within the chamber volume and the mixture external to the chamber. However, migration of water vapor through the membrane can be somewhat slow, thereby delaying the achievement of vapor pressure equilibrium. The time it takes for thermal equilibrium to be achieved is proportional to the size of the chamber volume. Thus it is preferable that the chamber volume be small, preferably in the range of 0.2 to 10.0 ml, and even more preferably in the range of 0.5 to 2.0 ml. A large chamber volume would result in a slow response in accurate relative humidity measurements. More specifically, it is the ratio of the area of the membrane to the volume of the chamber volume which determines the equilibration rate. Assuming a cylindrical chamber and circular membrane, the area of the circular membrane rises with the square of its diameter while the volume of the chamber volume rises with the cube of the membrane diameter, thus, it is highly advantageous to minimize the chamber diameter for a fixed chamber height.

It is preferable that the internal surfaces of the chamber that form the chamber volume be constructed of a nonabsorbent material, such as a metal. In order to accomplish this, the chamber is preferably entirely constructed of the nonabsorbent material. Alternatively, the chamber can be constructed of another suitably rigid material and the internal surfaces of the chamber can be coated with the nonabsorbent material. By entirely constructing the chamber of a nonabsorbent material, or by coating the internal surfaces of the chamber with the nonabsorbent material, inaccuracies in the relative humidity reading within the chamber volume due to water vapor being absorbed into the internal surfaces of the chamber are minimized. Acceptable nonabsorbent materials include brass, gold, tin, bronze, silver, platinum, and lead. However, the invention is not limited to any specific nonabsorbent material and other suitable nonabsorbent materials will be readily know by those skilled in the art.

The first temperature sensor that produces the second signal relating to temperature of the mixture within the chamber volume can be located either within the chamber volume itself or at a position exterior to the chamber that is at a temperature that is approximately the same as the temperature of the mixture within the chamber volume.

It is preferable that the apparatus be incorporated into a hand held weather instrument for measuring the relative humidity of air. In this embodiment, the apparatus will further comprise a plastic housing having an internal volume and a breather hole. The chamber is mounted in the internal volume of the housing so that the membrane is aligned with the breather hole. In this embodiment, the first temperature sensor can be located exterior to the chamber but within the internal volume of the housing. An O-ring can be positioned between the membrane and the housing that forms a sealed fit between the membrane and the housing. This allows the air surrounding the housing to be in contact with the membrane while affording additional protection to the chamber, the humidity sensor, and the interior of the instrument. It is further preferable in this embodiment that the second temperature sensor be located exterior to the internal volume of the housing, for example, in a passageway extending through the housing.

To minimize temperature induced errors, it is preferable that the first and second temperature sensors be a pair of precision thermistors, specified to track to within 1% resistance or 0.2° C. temperature. To further reduce errors, a single signal conditioning circuit which alternately polls one and then the other temperature sensor can be used. In this manner, errors associated with the temperature measurement circuitry are minimized. In an alternative embodiment the first temperature sensor and the humidity sensor can be combined so as to be located on a single substrate. A further example of an acceptable temperature sensor type is a platinum resistance device. Platinum resistance devices may be preferable from a functioning standpoint because these devices do not incorporate water absorbent material (unlike thermistors where the active element is encapsulated in epoxy resin), however, platinum resistance devices are more expensive and can be less sensitive. The present invention is not limited to any specific type of temperature sensor.

The chamber is preferably cylindrical in shape and has a first end and a second end. In this embodiment, the membrane preferably forms the first end of the chamber while a portion of a circuit board forms the second end of the chamber. It is further preferred that the portion of the circuit board that forms the second end of the chamber be constructed or coated with a nonabsorbent material, such as those described above. Grounding the chamber will solve electrostatic discharge problems.

In another aspect, the invention is an apparatus for obtaining measurements of a mixture comprising: a chamber having internal surfaces constructed of nonabsorbent material, the internal surfaces forming a chamber volume; an opening in the chamber; a membrane covering the opening, the membrane being permeable to water vapor while impermeable to liquid water; and a humidity sensor in the chamber volume for producing a first signal relating to relative humidity of the mixture within the chamber volume.

The apparatus of this aspect of the invention preferably further comprises a first temperature sensor for producing a second signal relating to temperature of the mixture within the chamber volume. The humidity sensor and first temperature sensor are adapted to be coupled to a processor capable of receiving a set of signals comprising the first and second signals.

In this aspect, the invention can be used in conjunction with other devices and/or instrumentation to achieve the desired results. It is also preferable that the apparatus further comprise the processor, the processor coupled to the humidity sensor and the first temperature sensor and programmed to calculate relative humidity of the mixture at a point as a function of the set of signals. When the point in the mixture for which the relative humidity is to be obtained is exterior to the chamber, a second temperature sensor will be included for producing a third signal relating to temperature of the mixture at that point. In this embodiment, the processor is also coupled to the second temperature sensor and the set of signals will further comprise the third signal. This aspect of the invention can further include any and all of the specifics set forth above.

In yet another aspect, the invention is a method of measuring relative humidity of a mixture comprising the steps of: providing an apparatus having a chamber having a chamber volume and an opening, a membrane covering the opening, the membrane being permeable to water vapor while impermeable to liquid water; measuring humidity of the mixture within the chamber volume with a first sensor; measuring temperature of the mixture within the chamber volume with a second sensor; measuring temperature of the mixture at a point exterior to the chamber with a third sensor; and calculating relative humidity of the mixture at the point exterior to the chamber with a processor as a function of the measurements obtained by the first sensor, the second sensor, and the third sensor.

It is preferred that the chamber used to perform the method of the invention be designed as set forth above in relation to the apparatus of the invention. In order to avoid redundancy, the structure of the preferred apparatus to be used in the method will be omitted.

MODES FOR CARRYING OUT THE INVENTION

Figure 1:
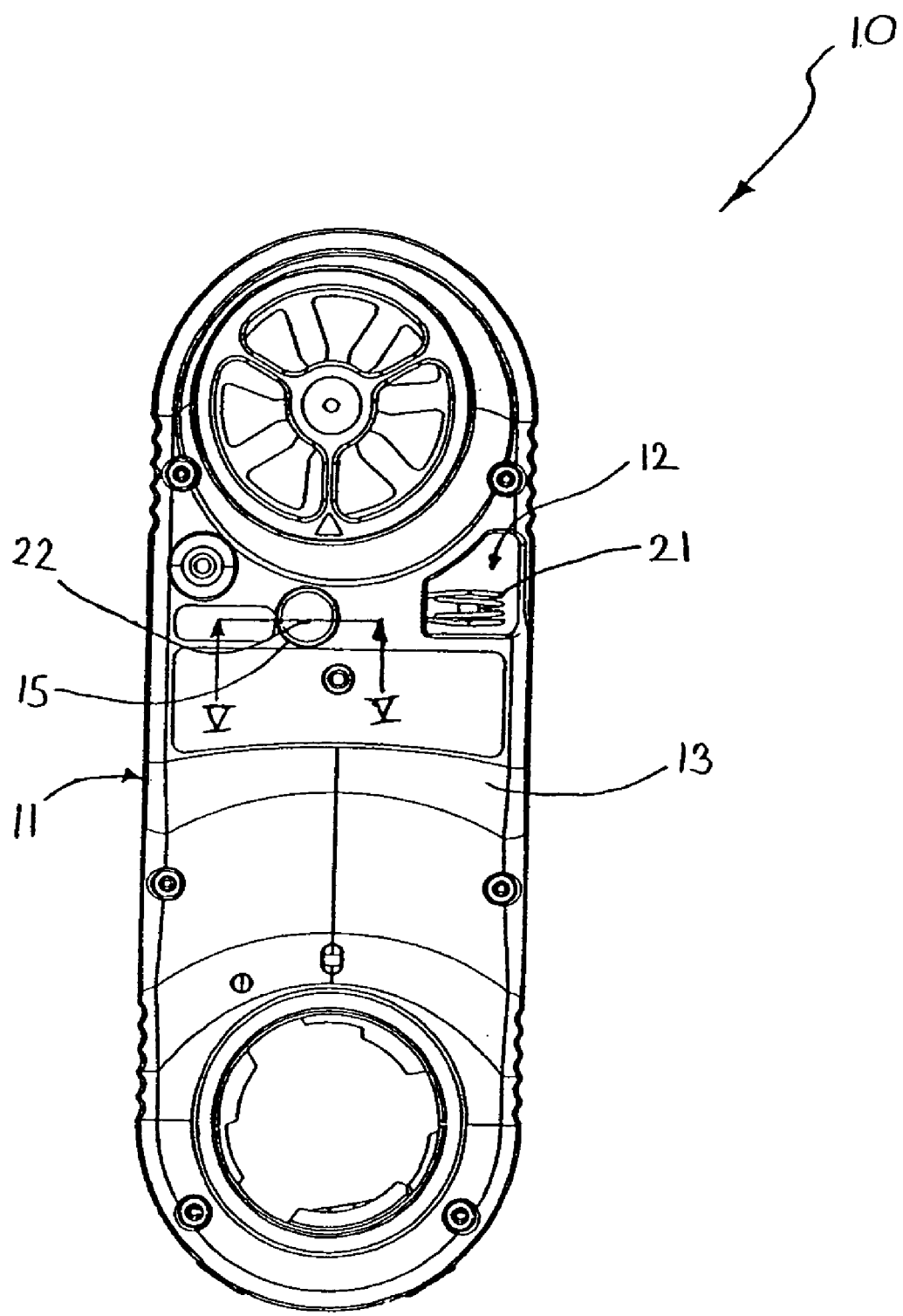
FIG. 1 is rear view of a hand held weather instrument incorporating a relative humidity sensing system according to an embodiment of the present invention.

Humidity is the amount of water in the vapor phase present in a gaseous mixture. Humidity is often expressed as relative humidity. Relative humidity is the amount of moisture by weight in a unit volume of a gas mixture relative to the amount which that mixture could hold if completely saturated at the mixture temperature. When the relative humidity is unity, the mixture is saturated. Relative humidity may also be expressed as percent relative humidity (% RH) in a mathematical relationship as follows:

$$\% RH = \frac{e}{e_w} * 100 \quad (2)$$

where
$e_w$=saturation pressure at the mixture temperature T; and
e=the vapor pressure at the mixture temperature T.

With this relationship, the indicated relative humidity $RH_C$ of a mixture within the chamber volume and the true relative humidity $RH_A$ of the mixture exterior to the chamber can be expressed respectively as follows:

$$RH_C = \frac{e_C}{ew_C}; \quad (3)$$

and $$RH_A = \frac{e_A}{ew_A} \quad (4)$$

where
$e_C$=the vapor pressure of the mixture at the temperature within the chamber;
$ew_C$=the saturation vapor pressure of the mixture at the temperature within the chamber;
$e_A$=the vapor pressure of the mixture at the temperature exterior to the chamber; and
$ew_A$=saturation vapor pressure of the mixture at the temperature exterior to the chamber.

If vapor pressure equilibrium is achieved so that the mixture within the chamber is as the same vapor as the mixture exterior to the chamber, equations (3) and (4) may be combined to solve for $RH_A$, thus, resulting in:

$$RH_A = RH_C \left[ \frac{ew_C}{ew_A} \right] \quad (5)$$

The values of the saturation vapor pressures $ew_C$ and $ew_A$ for various gases, including air, can be obtained from available tables, such as from Table 94, "Saturation Vapor Pressure over Water with Temperature," Smithsonian Meteorological Tables, 6th Revised Edition by Robert J. List, Smithsonian Institute, Washington, D.C. 1958. Accordingly, it is possible to determine the relative humidity of the air at a point external to the chamber by measuring the relative humidity within the chamber $RH_C$, the temperatures within the chamber $T_C$, and the temperature at the point exterior to the chamber $T_A$. It is not necessary for the user to wait for the temperature probe within the chamber to reach thermal equilibrium with the point external the chamber. It is in this way that an embodiment of the present invention can compensate for thermal lag.

Figure 2:
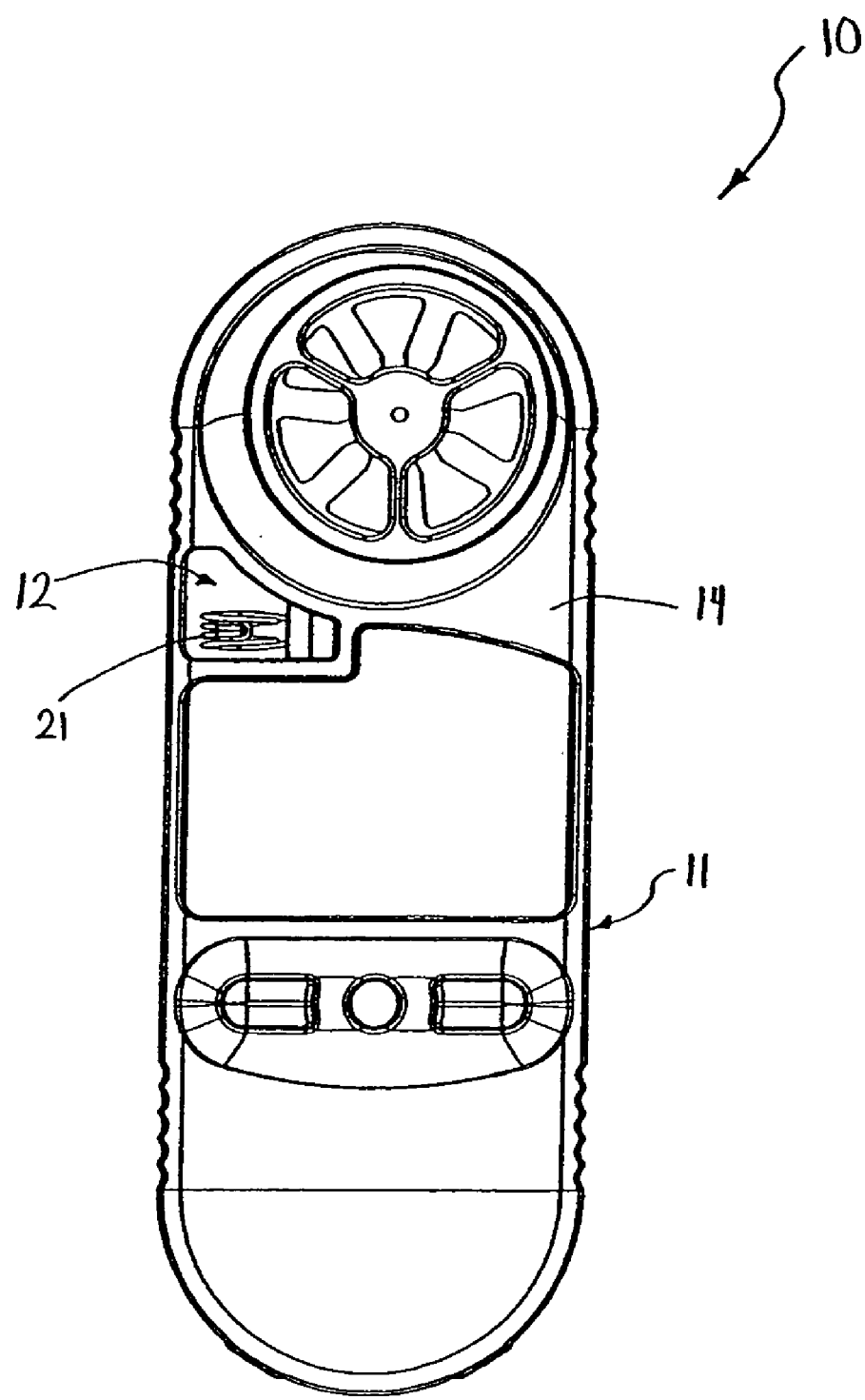
FIG. 2 is a front view of the hand held weather instrument of FIG. 1.
Figure 3:
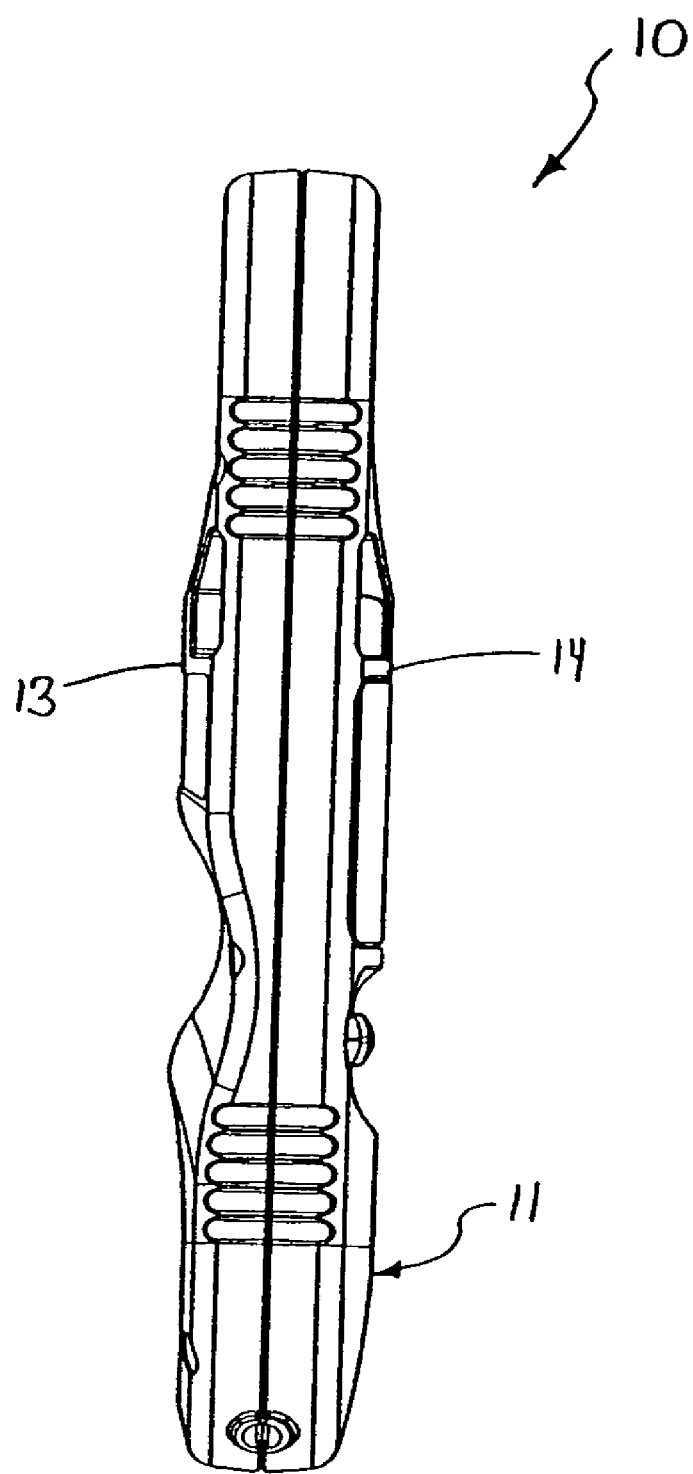
FIG. 3 is a side view of the hand held weather instrument of FIG. 1.

Referring now to the drawings, wherein like reference numerals designate corresponding structure throughout the views, and referring in particular to FIG. 1-3, there is shown hand held weather instrument 10. Weather instrument 10 is preferably small enough so that it is portable and can be held in a single hand. Weather instrument 10 comprises a housing 11 that forms an internal volume. Housing 11 is preferably constructed of plastic and manufactured using a molding process. However, other known techniques of manufacturing and other suitable materials of construction may be employed.

Housing 11 has passageway 12 extending therethrough. Passageway 12 extends through rear surface 13 and front surface 14 of housing 11 so that the surrounding air (i.e. the ambient air) can freely flow therethrough. Ambient thermistor 21 is positioned within passageway 12. Passageway 12 is sized so that ambient thermistor 21 can fit fully therein and not protrude beyond front and rear surfaces 13, 14 of housing 11 (best illustrated in FIG. 3). This provides protection to ambient thermistor 21 from physical damage while allowing ambient thermistor 21 to be directly exposed to the ambient air. Passageway 12 has walls that close passageway 12 off from the internal volume of housing 11.

Housing 11 further comprises breather hole 15 on rear surface 13. Breather hole 15 is an opening through rear surface 13 that provides access to the internal volume of housing 11. Breather hole 15 is preferably circular but can be any shape. As will be discussed below, breather hole 15 is aligned with and covered by membrane 22 of relative humidity sensing 20, which is housed within the internal volume of housing 11

Figure 4:
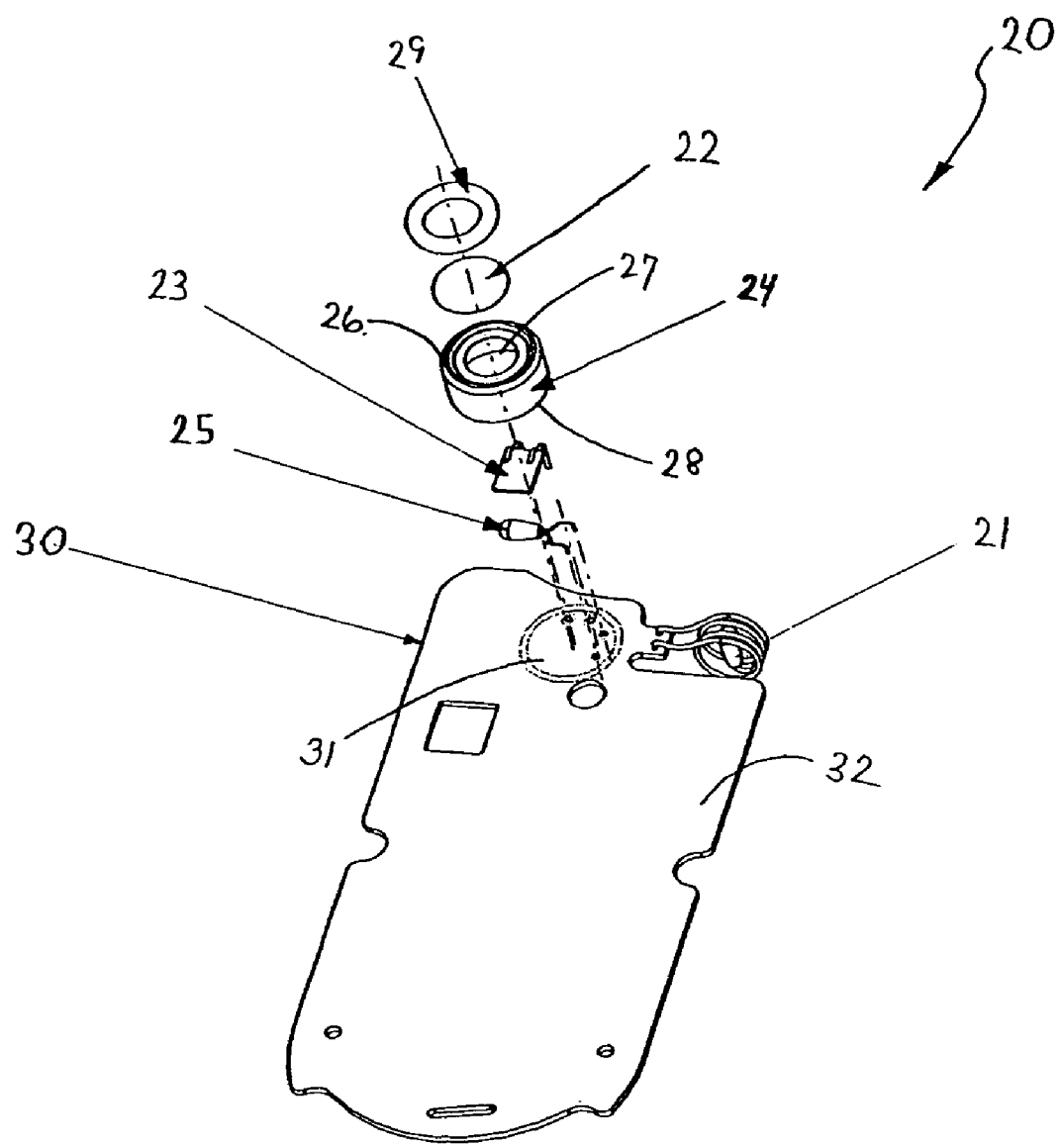
FIG. 4 is an exploded view of an embodiment of the relative humidity sensing system according to the present invention with the housing of the hand held weather instrument of FIG. 1 removed.
Figure 6:
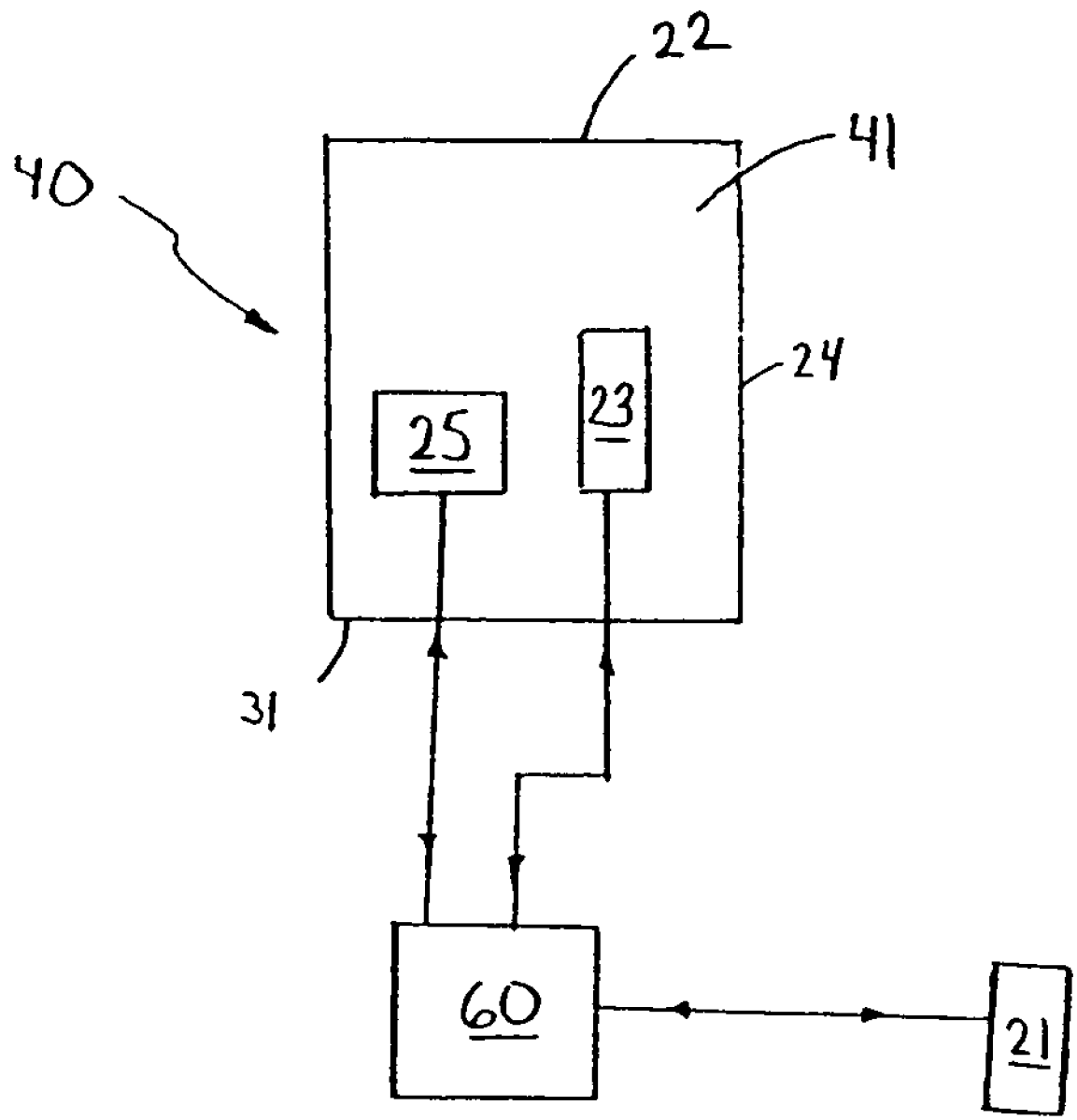
FIG. 6 is a block diagram of the circuit for the humidity sensing system of FIG. 4.

Referring now to FIG. 4, relative humidity sensing system 20 is illustrated in an exploded view. Relative humidity sensing system 20 comprises ambient thermistor 21, chamber thermistor 25, cylindrical tube 24, membrane 22, and humidity sensor 25. Ambient thermistor 21 is operably coupled to printed circuit bard 30 at a position so that when printed circuit board 30 is placed in the internal volume of housing 11, ambient thermistor 21 is positioned within passageway 12 (as illustrated in FIG. 1). When housing 11 is assembled with relative humidity sensing system 20 in the internal volume, the leads of ambient thermistor 21 will pass through one of the walls of passageway 12, allowing ambient thermistor 21 to remain operably coupled to processor 60 (FIG. 6).

Printed circuit board 30 has footprint 31 on its top surface 32. Footprint 31 is a coating of nonabsorbent material atop top surface 32. Footprint 31 is preferably a plating of gold. However, footprint 31 can be constructed of any nonabsorbent material, such as metals including brass, tin, bronze, silver, platinum, and lead. Footprint 31 is preferably sized so that cylindrical tube 24 can fit fully thereon. Footprint 31 has a plurality of holes electrically isolated from footprint 31 in the event that footprint 31 is conductive therein so that the leads of chamber thermistor 25 and humidity sensor 25 can extend therethrough and connect to the circuitry of printed circuit board 30, including processor 60 (FIG. 6).

Cylindrical tube 24 is secured to printed circuit board 30 atop footprint 31. Cylindrical tube 24 can be secured atop footprint 31 by soldering, brazing, through use of an adhesive, or any other means known in the art. Securing cylindrical tube 24 to printed circuit board 30 with solder or an electrically conductive adhesive such as silver loaded epoxy provides grounding, which solves electrostatic discharge problems. Cylindrical tube 24 is preferably constructed entirely of a nonabsorbent material, most preferably brass. Alternatively, cylindrical tube 24 can be constructed of any suitably rigid material and the internal surfaces of cylindrical tube 24 that form chamber volume 41 can be coated with the nonabsorbent material. Acceptable nonabsorbent materials include metals, specifically including gold, tin, bronze, silver, platinum, and lead.

Membrane 22 is positioned atop cylindrical tube 24 so as to cover opening 27 at top end 26 of cylindrical tube 24. Membrane 22 is constructed of a thin material that is permeable to gases but impermeable to liquids. More specifically, membrane 22 is constructed of material that is permeable to water vapor and impermeable to liquid water. Preferably, membrane 22 is constructed of a microporous hydrophobic polymeric material, but can be constructed of any material that allows gas to pass therethrough while preventing the passage of liquids, such as, for example, fibrous polytetraflouroethylene. Membrane 22 can be kept in place atop cylindrical tube 24 via adhesion, compression fit, or any other means known in the art.

Figure 5:
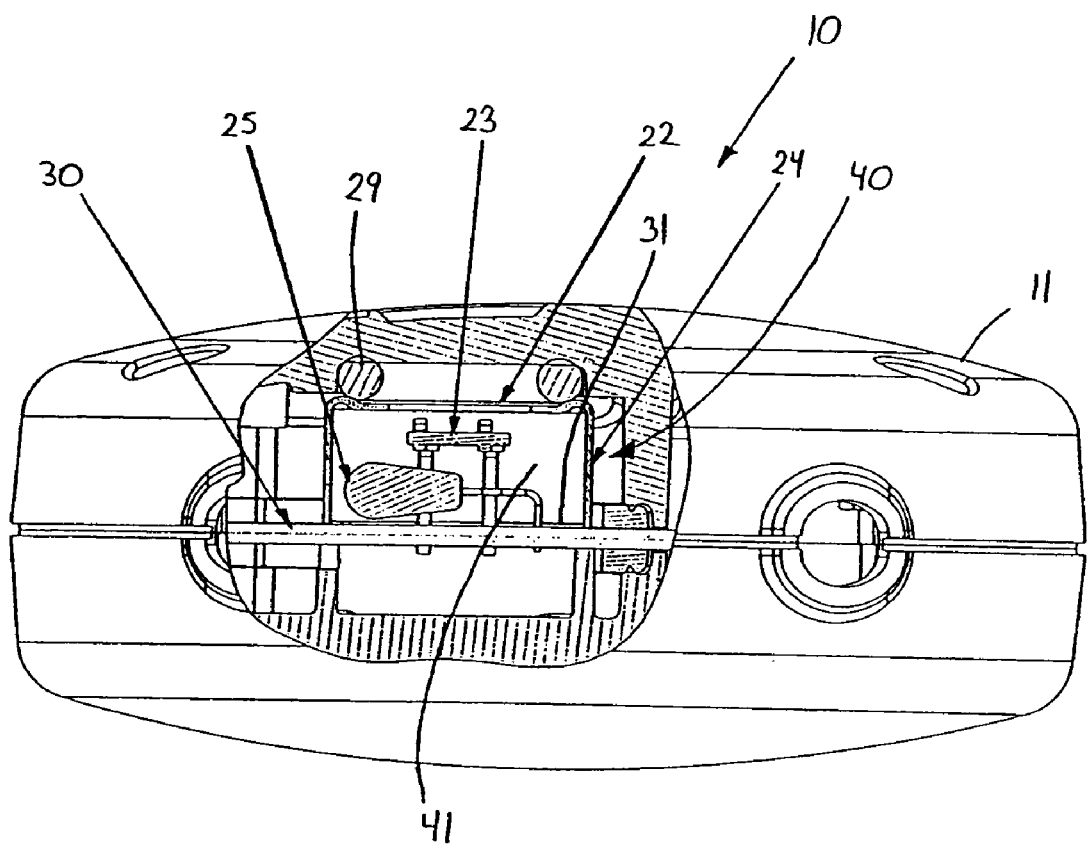
FIG. 5 is a cutaway view of the hand held weather instrument of FIG. 1 along line V-V showing the chamber of the relative humidity sensing system of FIG. 4 in cross-section.

When assembled, bottom end 28 of cylindrical tube 24 is secured atop footprint 31 while membrane 22 is secured to top end 26 of cylindrical tube 24 to form chamber 40 (FIG. 5). O-ring 29 helps hold membrane 22 atop cylindrical tube 24 when assembled in housing 11 of weather instrument 10.

Referring now to FIG. 5, chamber 40 forms a chamber volume 41. Chamber volume 41 is defined by the internal wall of cylindrical tube 24, the top surface of footprint 31, and the bottom surface of membrane 22. Footprint 31 forms one end of chamber 40 while membrane 22 forms the other end. Preferably, all of the internal surfaces that define chamber volume 41 are constructed of nonabsorbent material. As used herein, construction includes coating and/or plating.

Chamber thermistor 25 and humidity sensor 23 are located within chamber volume 41. Chamber volume 41 is sized so as to be large enough to house humidity sensor 23 and chamber thermistor 25. However, the size of chamber volume 41 should be minimized to effectuate a fast realization of vapor pressure equilibrium. Chamber volume 41 is preferably in the range of approximately 0.2 to 10.0 ml, and more preferably in the range of approximately 0.5 to 2.0 ml. Because chamber volume 41 is very small, and because chamber 40 is sealed both to the printed circuit board 30, and to the housing 11, it takes very little time for relative humidity equilibration.

It should be noted that while chamber themistor 25 is illustrated as being located within chamber volume 41 itself, the invention is not so limited. Chamber thermistor 25 can be positioned at any space where the temperature is approximately equal to the temperature of the mixture within chamber volume 41. For example, when relative humidity sensing system 20 is placed within housing 11, chamber thermistor 25 can be located external to chamber 40 at a point within the internal volume of housing 11, such as on the opposite side of printed circuit board 30.

Referring now to FIGS. 1 and 5, humidity sensing system 20 (FIG. 4) is placed within the internal volume of housing 11. When humidity sensing system 20 is positioned in housing 11, ambient thermistor 21 is located within passageway 12 and membrane 22 is aligned with breather hole 15 in top surface 13 of housing 11 (best illustrated in FIG. 1). Membrane 22 is exposed to the ambient air surrounding the weather instrument 10 through breather hole 15. O-ring 29 is positioned between the internal surface of housing 11 and membrane 22. O-ring 29 forms a sealed fit between membrane 22 and housing 11, helping to seal the internal volume of housing 11 from the ambient air. O-ring 29 also holds membrane 22 tightly pressed against the top surface of cylindrical tube 24 so that liquid can not enter either the chamber volume 41, or the body of the instrument 10 through breather hole 15.

Referring now to FIG. 6, chamber thermistor 25, ambient thermistor 21, and humidity sensor 23 are electrically coupled to processor 60. Processor 60 is programmed to receive and process signals from chamber thermistor 25, ambient thermistor 21, and humidity sensor 23. Processor 60 can be any type of properly programmed microprocessor, such as those manufactured by Intel.

Chamber thermistor 25 and ambient thermistor 21 are preferably a pair of matched precision thermistors that track to within 1% resistance or 0.2° C. temperature. To further reduce errors, a single signal conditioning circuit which alternately polls one then the other temperature thermistor 25, 21 is used. The use of matched thermistors types for chamber thermistor 25 and ambient thermistor 21, and the use of the same measurement method, provides closer matching between the two temperature measurements than the specified ±1° C. overall accuracy of the thermistors. The matching is influenced largely by the accuracy specification of the thermistors, which is ±0.2° C. It is possible to use thermistors matched to ±0.1° C. for greater accuracy if necessary. Chamber thermistor 25 and ambient thermistor 21 are resistant type thermistors that have a known resistance/temperature characteristic from which temperature can be calculated by processor 60 by detecting variations in resistance. Thus, processor 60 can receive and processes signals from chamber thermistor 25 which indicate the temperature of the mixture within chamber volume 41 and from ambient thermistor 21 which indicate the temperature of the ambient mixture exterior to housing 11.

Humidity sensor 23 is a glass based polymeric capacitive sensor. The capacitance of humidity sensor 23 increases with the relative humidity of the mixture in which humidity sensor 23 is in contact with. Through the use of an electrical signal, processor 60 can monitor the capacitance of humidity sensor 23 and thus the humidity of the mixture within chamber volume 41. The relative humidity measurement preferably has a specified overall accuracy of at least ±3% RH.

Alternatively, a combined humidity/temperature sensor can be used to measure the temperature and relative humidity within chamber volume 41. In this embodiment, the temperature sensor and the humidity sensor are located on a single substrate. This embodiment is not believed to be optimal, providing less accurate readings.

All of these elements—a small isolated chamber housing both the humidity and temperature sensors, brass construction, gold plated printed circuit board, precision tracking thermistors, and a method of sealing the chamber to the housing so that the humidity sensor sees plastic only external to the membrane—combine to produce an instrument with a fast and accurate relative humidity response under the conditions anticipated for a hand held weather instrument.

As discussed above, hand held weather instruments often experience accuracy problems from thermal lag, i.e. the humidity sensor being at a different temperature than the mixture whose relative humidity is to be measured. Specifically there is a strong possibility that weather instrument 10 will be removed for instance from a pocket, or a warm house into a cold environment. This will result in humidity sensor 23 being at a temperature that is markedly different than the ambient air surrounding housing 11. Thus, a relative humidity measurement would be in error. This problem can be addressed, and thus the true relative humidity $RH_A$ of the ambient air can be calculated, by knowing the temperature $T_A$ of the ambient air, the temperature $T_C$ within the chamber volume, and the relative humidity $RH_C$ of the air within the chamber volume, then applying the correction algorithm set forth in equation (5) above.

The operation of weather instrument 10 to measure the relative humidity $RH_A$ of ambient air will now be described in detail with respect to FIGS. 1-6. Weather instrument 10 is first removed from its storage environment and placed in the ambient air environment. Ambient thermistor 21 and membrane 22 are in direct contact with the ambient air. Because chamber volume 41 is a very small volume, it takes very little time for relative humidity equilibration to occur between the air within chamber volume 41 and the ambient air.

Upon a user activating the relative humidity measuring mode of weather instrument 10, chamber thermistor 25 measures the temperature $T_C$ of the air within chamber volume 41, humidity sensor 23 measures the relative humidity of the air within chamber volume 41, and ambient thermistor 21 measures the temperature $T_A$ of the ambient air surrounding housing 11. Electrical signals relating to $T_C$ are transmitted to processor 60 from chamber thermistor 25 for processing. Electrical signals relating to $T_A$ are also transmitted to processor 60 from ambient thermistor 21 for processing. Preferably, a single signal conditioning circuit is used that alternately polls chamber thermistor 25 and ambient thermistor 21. Humidity sensor 23 also transmits electrical signals relating to $RH_C$ to processor 60 for processing.

Upon receiving the signals from chamber thermistor 25, ambient thermistor 21, and humidity sensor 23, processor 60, through proper programming, calculates the relative humidity $RH_A$ of the ambient air using stored values and the algorithmic relationship set forth in equation (5) above.

While the invention has been described and illustrated in sufficient detail that those skilled in this art can readily make and use it, various alternatives, modifications, and improvements should become readily apparent without departing from the spirit and scope of the invention. Specifically, the present invention is not limited to use in air but can be used in any mixture where relative humidity can be measured. Moreover, the present invention is not limited to hand held weather meters but can be incorporated into a variety of weather instruments or it can be used on its own, independent of a housing or other structure.

What is claimed is:

1. A method for calculating the relative humidity of a mixture comprising:
   measuring a chamber relative humidity ($RH_C$) within a chamber enclosing an humidity sensor;
   measuring a first temperature ($T_C$) within the chamber;
   measuring a second temperature ($T_A$) separate from said chamber, said second temperature being the temperature of the mixture; and
   calculating the mixture relative humidity ($RH_A$) based on the chamber relative humidity, a first value representing the first temperature and a second value representing the second temperature.

2. The method of claim 1, wherein the mixture is ambient air.

3. The method of claim 1 further comprising the step of transmitting each of the first temperature, second temperature and chamber relative humidity to a processor, said processor thereby calculating the mixture relative humidity.

4. The method of claim 3, wherein said first value is a known saturation vapor pressure ($ew_C$) for the first temperature $T_C$, and said second value is a known saturation vapor ($ew_A$) for the second temperature $T_A$.

5. The method of claim 4, wherein the calculating step is in accordance with the formula $RH_A = RH_C[ew_C/ew_A]$.

6. An apparatus for obtaining measurements of a mixture comprising:
   a chamber having a chamber volume and an opening;
   a humidity sensor in the chamber volume for producing a first signal relating to relative humidity within the chamber volume;

a first temperature sensor for producing a second signal relating to the temperature within the chamber volume ($T_C$);

a second temperature sensor for producing a third signal relating to the temperature of the mixture at a point exterior to the chamber ($T_A$); and a processor, coupled to the humidity sensor, the first temperature sensor, and the second temperature sensor, for receiving the first, second, and third signals, and calculating a relative humidity of the mixture from said first signal, a first value representing the second signal and a second value representing the third signal.

7. The apparatus of claim 6 wherein internal surfaces of the chamber are constructed of a nonabsorbent material.

8. The apparatus of claim 6 wherein the first temperature sensor is located within the chamber volume.

9. The apparatus of claim 6 wherein the humidity sensor and the first temperature sensor are combined on a single substrate located within the chamber volume.

10. The apparatus of claim 6 wherein the chamber volume is approximately 0.5 to approximately 2.0 ml.

11. The apparatus of claim 6, wherein said first value is a known saturation vapor pressure ($ew_C$) for the second signal, and said second value is a known saturation vapor ($ew_A$) for the third signal.

12. The apparatus of claim 11, wherein the processor calculate the relative humidity of the mixture in accordance with the formula $RH_A = RH_C[ew_C/ew_A]$.

13. The apparatus of claim 6 wherein the first temperature sensor and the second temperature sensor are thermistors.

14. The apparatus of claim 13 wherein the thermistors are matched.

15. The apparatus of claim 6 wherein the chamber is cylindrically shaped having a first end and a second end, the membrane forming the first end of the chamber and a portion of a circuit board forming the second end of the chamber.

16. The apparatus of claim 15 wherein the portion of the circuit board that forms the second end of the chamber is coated with or constructed of a nonabsorbent material.

17. The apparatus of claim 16 wherein the nonabsorbent material is selected from the group consisting of brass, gold, tin, bronze, silver, platinum, and lead.

18. The apparatus of claim 6 further comprising a membrane, permeable to water vapor while impermeable to liquid water, covering the opening of the chamber.

19. The apparatus of claim 18 wherein the chamber is entirely constructed of the nonabsorbent material or the internal surfaces are a coating of nonabsorbent material.

20. The apparatus of claim 18 wherein the nonabsorbent material is a metal.

21. The apparatus of claim 18 wherein the nonabsorbent material is selected from the group consisting of brass, gold, tin, bronze, silver, platinum, and lead.

22. The apparatus of claim 18 wherein the membrane is constructed of microporous hydrophobic polymeric material.

23. The apparatus of claim 18 further comprising a housing having an internal volume and a hole; the chamber mounted in the internal volume of the housing so that the membrane is aligned with the hole; the second temperature sensor being located exterior to the internal volume of the housing; the first temperature sensor being located exterior to the chamber but within the internal volume of the housing; an O-ring positioned between the membrane and the housing so as to form a sealed fit between the membrane and the housing; the second temperature sensor located in a passageway extending through the housing; wherein the first temperature sensor and the second temperature sensor are matched thermistors; wherein the chamber volume is in the range from approximately 0.5 to approximately 2.0 ml; and wherein the chamber is constructed of a metal.

24. The apparatus of claim 18 further comprising:

a housing having an internal volume and a breather hole;

wherein the chamber is mounted in the internal volume of the housing so that the membrane is aligned with and in fluid communication with the breather hole; and the second temperature sensor being located exterior to the internal volume of the housing.

25. The apparatus of claim 24 wherein the first temperature sensor is located exterior to the chamber but within the internal volume of the housing.

26. The apparatus of claim 15 further comprising an O-ring positioned between the membrane and the housing so as to form a sealed fit between the membrane and the housing.

27. The apparatus of claim 24 wherein the second temperature sensor is located in a passageway extending through the housing.

28. The apparatus of claim 24 wherein the housing is adapted to be a hand held meter.

* * * * *